United States Patent [19]

Krylova et al.

[11] 4,065,958
[45] Jan. 3, 1978

[54] METHOD OF CONTROLLING PHYSICAL CHARACTERISTICS OF FLUID MEDIUM

[76] Inventors: Eleonora Dmitrievna Krylova, Beskudnikovsky pereulok, 32, korpus 2, kv. 32; Nikolai Ivanovich Brazhnikov, ulitsa Bebelya, 3, korpus 11, kv. 48, both of Moscow, U.S.S.R.

[21] Appl. No.: 733,384

[22] Filed: Oct. 18, 1976

[51] Int. Cl.² ............................................. G01N 29/02
[52] U.S. Cl. ..................................... 73/53; 73/623; 73/194 A
[58] Field of Search ............... 73/194 A, 67.5 R, 67.6, 73/53

[56] References Cited

U.S. PATENT DOCUMENTS

| 3,237,453 | 3/1966 | Yamamoto et al. | 73/194 A |
| 3,575,050 | 4/1971 | Lynnworth | 73/194 A |
| 3,782,193 | 1/1974 | Meyer et al. | 73/181 |
| 3,987,674 | 10/1976 | Baumoel | 73/194 A |

FOREIGN PATENT DOCUMENTS

| 151,053 | 1962 | U.S.S.R. | 73/194 A |

*Primary Examiner*—Charles A. Ruehl
*Attorney, Agent, or Firm*—Lackenbach, Lilling & Siegel

[57] ABSTRACT

A method of controlling physical characteristics of a fluid medium by transmitting ultrasonic vibrations to the medium under control through a sound conducting medium and through a pipe wall at an angle $\alpha$, acute or obtuse, to the pipe exterior, said angle being determined by the relationship:

$$\alpha = \arcsin C_o/(\sqrt{2} \cdot C)$$

where:
$C_o$ is the velocity of propagation of ultrasonic vibrations in the sound conducting medium; and
$C$ is the velocity of propagation of transverse ultrasonic vibrations in the material of the pipe wall.

Therewith, the frequency $f$ of the ultrasonic vibrations being transmitted is selected according to the relationship:

$$f = (n \cdot C)/(\sqrt{2} \cdot d)$$

where:
$n$ is an integer (such as 1, 2 or 3); and
$d$ is the thickness of the pipe wall.

Parameters of the ultrasonic vibrations, passed through the medium under control, are then measured and their value is used to determine the value of a parameter being controlled. The herein proposed method makes it possible to increase the accuracy of controlling physical characteristics of a fluid medium.

2 Claims, 3 Drawing Figures

METHOD OF CONTROLLING PHYSICAL CHARACTERISTICS OF FLUID MEDIUM

The present invention relates to ultrasonic velocity measuring and control systems used for automatic control of industrial processes, and more particularly to a method of controlling physical characteristics of fluid media.

The invention may find suitable application in the non-contact control of physical characteristics of a fluid medium, such as flow rate, pressure, density, etc., such control being applicable in chemical, aircraft, machine-building and other branches of industry.

When measuring physical characteristics of a fluid medium within pipeline systems, disturbances are liable to appear in the course of transmission of ultrasonic vibrations to the fluid under control through the pipe wall. These disturbances are caused by the reverberation of ultrasonic vibrations within the pipe wall and the pipe interior. The reverberation disturbances cause substantial errors in the measurement of the physical characteristics of a fluid medium.

To diminish the reverberation effect in the course of measuring physical characteristics of a fluid medium, and to increase the accuracy of measurement, which is of particular importance for measuring the speed of the fluid flow at short time intervals or the flow rate of fluid at small acoustic bases (the distances between the transmitter and receiver of ultrasonic vibrations), ultrasonic vibrations are transmitted to the medium under control at an angle, acute or obtuse, to the pipe exterior.

Known in the prior art is a method of measurement and control of physical characteristics of a fluid medium by using ultrasonic vibrations (cf. U.S. Pat. No. 2,826,912). This method consists of transmitting ultrasonic vibrations to the fluid under control through a sound conducting medium and through the pipe wall at an angle, acute or obtuse, to the pipe exterior. Parameters of ultrasonic vibrations, which have passed through the medium under control, are measured and their value is used to determine the value of the characteristic being controlled.

However, the prior-art method does not ensure a high accuracy of controlling physical characteristics of a fluid medium, such as the fluid density or velocity, in the event of substantial variations in the velocity of propagation of ultrasonic vibrations in the fluid. Less effective accuracy of control is caused by the appearance of an additional phase shift in ultrasonic vibrations during their transmission through the pipe wall. The phase shift value depends upon the acoustic characteristics of the sound conducting medium, the pipe wall and the fluid under control.

In addition, lower accuracy of control is brought about by measurement errors caused by the interference of acoustic disturbances with the informative signal. The acoustic disturbance is refered to herein to denote ultrasonic vibrations having passed from a transmitter directly along the pipe wall (over its periphery) to a receiver.

The present invention has as its object an increase in the accuracy of a method of the ultrasonic vibration control of physical characteristics of a fluid medium.

This object is accomplished in ultrasonic vibration control of physical characteristics of a fluid medium by transmitting ultrasonic vibrations to the medium under control within a pipe through the pipe wall at an angle, acute or obtuse, to the pipe exterior; parameters of the ultrasonic vibrations, which have passed through the medium under control and through the other sound conducting medium, are measured and their value is used to determine the value of the characteristic under control, the angle $\alpha$ of entry of the ultrasonic vibrations transmitted through the fluid under control, according to the invention, being established by the relationship:

$$\alpha = \arcsin C_o/(\sqrt{2} \cdot C)$$

where:
$C_o$ is the velocity of propagation of ultrasonic vibrations in the sound conducting medium; and
$C$ is the velocity of propagation of transverse ultrasonic vibrations in the pipe wall material, said ultrasonic vibrations having a frequency $f$ determined by the relationship:

$$f = (N \cdot C)/(\sqrt{2} \cdot d)$$

where:
$n$ is an integer (1, 2, 3 . . . ); and
$d$ is the thickness of the pipe wall.

The herein proposed method makes it possible to increase the accuracy of controlling physical characteristics of a fluid medium by using ultrasonic vibrations. Higher accuracy is attained by the elimination of an additional phase shift in ultrasonic vibrations during their transmission through the pipe wall, as well as by diminishing the error caused by the interference between the informative signal and acoustic disturbance, these positive factors being ensured by the above-mentioned angle of entry and by the frequency of ultrasonic vibrations used for this purpose.

These and other objects of the present invention and the manner of attaining them will become more apparent and the invention itself will be best understood by reference to the following description of an embodiment thereof taken in conjunction with the accompanying drawings, wherein.

Figure 1:
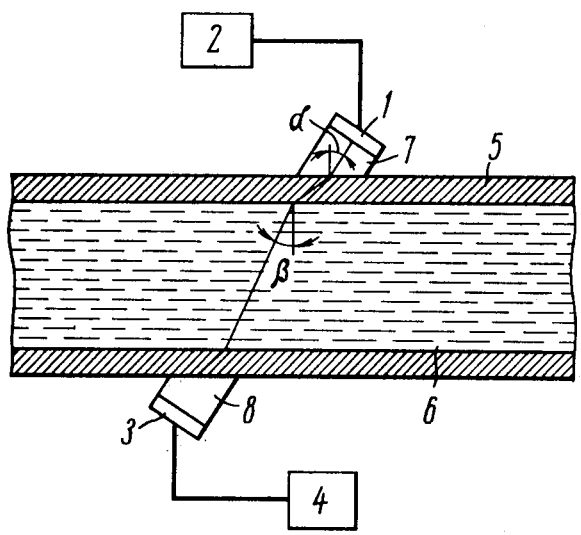
FIG. 1 shows an apparatus for carrying out a method of the ultrasonic vibration control of physical characteristics of a fluid medium (longitudinal sectional view of a pipe), according to the invention.

Referring now to the aforecited drawings the principle and operation of the invention is disclosed. An apparatus for carrying out a method of the ultrasonic vibration control of physical characteristics of a fluid medium comprises a transmitter 1 (FIG. 1) of ultrasonic vibrations, with an oscillator 2 coupled thereto, and a receiver 3 of ultrasonic vibrations, with a measuring unit 4 coupled thereto. The transmitter 1 and the receiver 3 of ultrasonic vibrations are of the same design and are wide-band transmitters and receivers of the piezoelectric type known in the art (cf. U.S. Pat. No. 3,287,692). The oscillator 2 is constructed in accordance with the known design of shock-exited oscillators (cf. U.S. Pat. No. 3,282,086). The measuring unit 4 is built using a conventional circuit (cf., for example U.S. Pat. No. 3,473,378).

Figure 2:
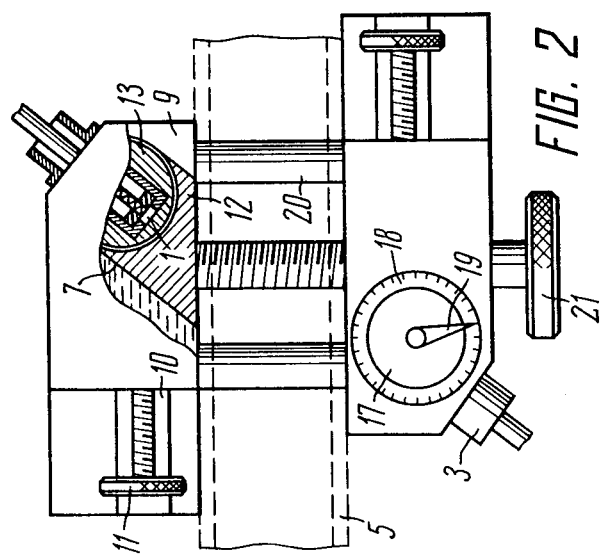
FIG. 2 shows a portion of a pipe with a transmitter and a receiver of ultrasonic vibrations being mounted thereupon (partial sectional view of the transmitter and of sonic guides), according to the invention.

The transmitter 1 and the receiver 3 of ultrasonic vibrations are acoustically coupled to a pipe 5, filled with a fluid 6 under control, with the help of sonic guides 7 and 8 respectively. Each sonic guide 7 and 8 is arranged in a casing 9 (FIG. 2) mounted on the pipe 5 and being movable along the axis of the pipe 5 along guide means 10. The guide means 10 is provided with a stop screw 11. The structure of the casing 9, as described hereinabove, makes it possible to use the herein disclosed apparatus for controlling characteristics of the fluid medium 6 within pipes 5 which may vary in diameter.

Each sonic guide 7 and 8 is fitted with a bushing 12 and a bushing 13. The bushing 12 is rigidly fixed in the casing 9 and contacts the outer surface of the pipe 5 through a thin layer 14 of the fluid. The bushing 13 is acoustically coupled to the transmitter 1 or the receiver 3 of ultrasonic vibrations, and is mounted turnably about an axis which is perpendicular to the axis of the bushing 12. Mounted on the axle of the bushing 13 is a handle 15 (FIG. 3) with an index pin 16.

Figure 3:
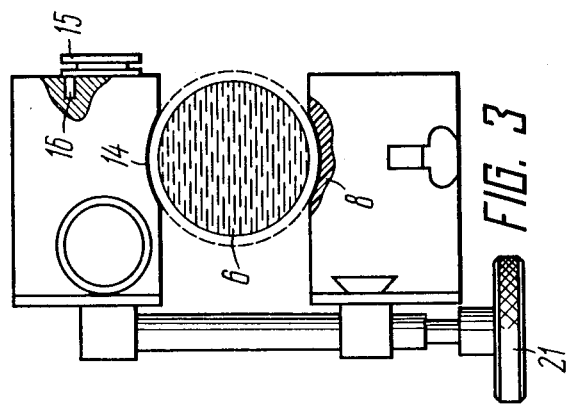
FIG. 3 is a side elevation view, similar to FIG. 2 according to the invention.

Mounted on the surface of the casing 9 is a dial 17 (FIG. 2) having a scale 18, graduated in degrees, and a pointer 19 kinematically associated with the handle 15 (FIG. 3).

Due to the proposed structure of the sonic guides 7 and 8 (FIG. 1), making for variations in the angle of inclination depending upon the pipeline material, the herein disclosed apparatus can be used for carrying out control of physical characteristics of a fluid medium within pipes 5 made from various materials.

The casings 9 (FIG. 2), with the sonic guides 7 and 8 arranged therein, are mounted on the pipe 5 with the help of guides 20 and a clamping screw 21.

In view of the fact that the transmitter 1 and the receiver 3 are mounted on the pipe 5 with the aid of the sonic guides 7 and 8, which are not made part of the pipe 5, the herein proposed apparatus may be used for the non-destructive control of physical characteristics of a fluid medium in closed lines. This speeds up the process of control and cuts down the expences involved.

A method of the ultrasonic vibration control of physical characteristics of a fluid medium is carried out with the use of the hereinabove described apparatus in the following way.

The oscillator 2 (FIG. 1) delivers electric pulses to the transmitter 1 which operates to convert the electric pulses into mechanical ultrasonic vibrations. The transmitter 1 transmits these ultrasonic vibrations to the sonic guide 7, the frequency $f$ of these vibrations being established in accordance with the relationship:

$$f = (n \cdot C)/(\sqrt{2} \cdot d) \quad (1)$$

where:
$n$ is an integer;
$d$ is the wall thickness of the pipe 5; and
$C$ is the velocity of propagation of transverse ultrasonic vibrations in the pipe wall material.

The transmitted ultrasonic vibrations pass through the sonic guide 7 and through the wall of the pipe 5 into the fluid 6 under control at an angle $\alpha$, adjusted for a given measurement by the handle 15 (FIG. 3), and determined from the relationship:

$$\alpha = \arcsin C_o/(\sqrt{2} \cdot C) \quad (2)$$

where:
$C_o$ is the velocity of propagation of ultrasonic vibrations in the material of the sonic guides;
$C$ is the velocity of propagation of transverse ultrasonic vibrations in the pipe wall material.

The ultrasonic vibrations passing into the fluid 6, propagate therein at an angle $\beta$ which depends upon the velocity $C_1$ of propagation of ultrasonic vibrations in the fluid 6 under control, and is determined by the relationship:

$$\sin \beta = (C_1 \cdot \sin\alpha)/C_o \quad (3)$$

After passing through the fluid 6, the ultrasonic vibrations enter through the wall of the pipe 5 the sonic guide 8 of the receiver 3 of ultrasonic vibrations at the angle $\alpha$ with a time shift relative to the moment of transmission, which depends upon the velocity of their propagation in the fluid 6.

The time shift of the ultrasonic vibrations received by the receiver 3 is measured by a phase meter (not shown) of the measuring unit 4, and the value thereof is used to determine the value of a fluid physical characteristic being controlled, such as its density or pressure.

Where it is necessary to control the speed of the fluid flow, additional counter transmission of a second ultrasonic wave is carried out by the receiver 3, and the measuring unit 4 is used to measure the time shift difference of the received signals. It is therefore the value of this time shift difference which is used to determined the velocity of the fluid flow.

The hereinabove described method makes it possible to increase the accuracy of ultrasonic vibration control of physical characteristics of a fluid medium. An increase in the accuracy is attained by eliminating an additional phase shift of ultrasonic vibrations when they are transmitted throught the pipe wall, and by diminishing the error caused by interference between the informative signal and acoustic disturbance, as explained hereinbelow.

With ultrasonic vibrations being directly transmitted through the wall of the pipe 5, there appears an additional phase shift of ultrasonic vibrations which is equal to half the phase difference of two vibrations at each point of entry of ultrasonic vibrations of the surface of the pipe 5. One of the waves is incident on a given point from the transmitter 1, while the other is echoed back there after double reflection within the wall of the pipe 5. The phase shift is expressed by the equation:

$$\phi_t = \frac{2\pi f \cdot d}{C} \sqrt{1 - \frac{C^2}{C_o^2} \sin^2\alpha} \ \beta \quad (4)$$

For the angles of entry $\alpha$ selected according to relationship (2), the phase shift is a multiple of $\pi$. Further, the echo and direct ultrasonic waves will always be in phase, with a phase difference between them being $2n\pi$, said waves reinforcing each other at the point of exit of ultrasonic vibrations from the wall of the pipe 5. Due to multiple superimposition of these in-phase ultrasonic vibrations, there occurs a resonance in the wall of the pipe 5, which results in a maximum rate of signal propagation through the wall. Therefore, the ultrasonic vibrations pass into the fluid 6 from the sonic guide 7 through the wall of the pipe 5 in a manner (in the function of transmission) such as if these vibrations were transmitted from the sonic guide 7 directly to the fluid 6 under control and no wall were present.

Insofar as the phase shift $\phi t$ is likewise dependant upon the frequency $f$ of ultrasonic vibrations, it is possible to obtain the requisite value $\phi = k\pi$ by adjusting the frequency $f$ at a constant thickness $d$ of the wall of the pipe 5, which makes for the maximum rate of propagation of ultrasonic vibrations from the sonic guide 7 into the fluid 6 through the wall of the pipe 5. If, however, the choice of the frequency $f$ is inappropriate, for example, the phase shift thereby created is equal to an odd number $\pi/2$, the ultrasonic vibrations will be damped in the wall will not pass into the fluid 6.

When ultrasonic vibrations are transmitted from sonic guides 7 and 8 made from a material similar to that of the pipe 5, as is the case in conventional systems wherein a material is built up upon the wall of the pipe 5, the reflections of ultrasonic vibrations in the boundary region between the sonic guide 7 and the pipe 5 are eliminated. In this event there is no amplification of a signal (due to the fact that the proposed apparatus is capable of multiple integration of in-phase ultrasonic vibrations, both transmitted thereinto and reflected therefrom) which diminishes transmission of ultrasonic energy into a fluid.

In the herein proposed apparatus, the material used for the sonic guides 7 and 8 and that used for the pipe 5 differ as to their acoustic impedance, which means that there will always be a reflection of ultrasonic vibrations in the boundary region between the sonic guide 7 and the wall of the pipe 5. This in turn ensures the maximum rate of propagation of ultrasonic vibrations with $\alpha$ and $f$ being selected such that the in-phase relationship of the reflected and transmitted ultrasonic vibrations will be provided.

What is claimed is:

1. A method of controlling physical characteristics of a fluid medium by ultrasonic vibrations comprising the following steps: transmitting said ultrasonic vibrations into said fluid medium under control through a sound conducting medium within a pipe and through a wall of said pipe at an angle $\alpha$, other than 90°, to said pipe exterior, said angle $\alpha$ being determined from the relationship:

$$\alpha = \arcsin C_o/(\sqrt{2} \cdot C)$$

$C_o$ is the velocity of propagation of said ultrasonic vibrations in said sound conducting medium, and $C$ is the velocity of propagation of transverse ultrasonic vibrations within the material of said wall of said pipe, the frequency $f$ of said vibrations being determined from the relationship:

$$f = (n \cdot C)/(\sqrt{2} \cdot d)$$

where $n$ is an integer, and $d$ is the thickness of said wall of said pipe; and measuring parameters of said ultrasonic vibrations which have passed through said fluid medium under control and through another sound conducting medium, with the purpose of using the value thereof to determine the value of said characteristic being controlled.

2. The method of controlling physical characteristics of a fluid medium by ultrasonic vibrations according to claim 1, wherein the material used for the sound conducting mediums is of a different acoustic impedance than the material used for the pipe.

* * * * *